United States Patent [19]

Hohmann et al.

[11] Patent Number: 5,158,974
[45] Date of Patent: Oct. 27, 1992

[54] PREPARATION OF N-ALKYL- AND N,N-DIALKYLDIAMINOETHANES

[75] Inventors: Andreas Hohmann, Ludwigshafen; Wolfgang Reuther, Heidelberg; Werner Bochnitschek, Ludwigshafen, all of Fed. Rep. of Germany

[73] Assignee: BASF Aktiengesellschaft, Ludwigshafen, Fed. Rep. of Germany

[21] Appl. No.: 597,047

[22] Filed: Oct. 15, 1990

[30] Foreign Application Priority Data

Oct. 13, 1989 [DE] Fed. Rep. of Germany ....... 3934191

[51] Int. Cl.$^5$ ............................................. C07C 209/62
[52] U.S. Cl. .................................... 564/487; 564/511
[58] Field of Search ..................... 564/487, 511, 467

[56] References Cited

U.S. PATENT DOCUMENTS

| | | | |
|---|---|---|---|
| 2,318,729 | 5/1943 | Wilson | 260/383 |
| 3,674,844 | 7/1972 | Shen et al. | 564/184 |
| 4,942,260 | 7/1990 | Laurenzo et al. | 564/298 |

OTHER PUBLICATIONS

Suzuki et al I, Chem. Abstr., vol. 109, 230269t (1988).
Suzuki et al II, Chem. Abstr., vol. 109, 230270m (1988).
Chem. Abstr. vol. 96, 180762p Jan. 1982.
Chem. Abstr. vol. 99, 157814k Mar. 1983.
Chem. Abstr. vol. 98, 157813p 1983.

*Primary Examiner*—Richard L. Raymond
*Assistant Examiner*—Brian M. Burn
*Attorney, Agent, or Firm*—John H. Shurtleff

[57] ABSTRACT

A process is described for the preparation of an N-alkyl- or N,N-dialkyl-1,2-diaminoethane of the general formula I

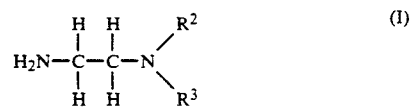

where $R^1$ is hydrogen or methyl, $R^2$ is $C_1$- to $C_5$-alkyl, and $R^3$ is hydrogen or $C_1$- to $C_5$-alkyl, with the proviso that the total number of carbon atoms in $R^2$ and $R^3$ is an integer from 1 to 6, by reacting an imine of the general formula II

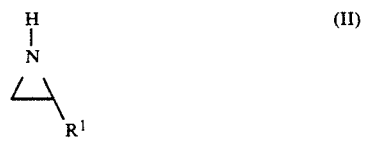

with an amine of the general formula III

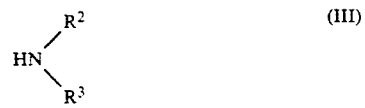

where $R^1$, $R^2$ and $R^3$ are as defined above, which comprises carrying out the reaction in the presence of carbon dioxide at from 10° to 150° C. and at from 0.5 to 50 bar.

11 Claims, No Drawings

PREPARATION OF N-ALKYL- AND N,N-DIALKYLDIAMINOETHANES

The present invention relates to a novel and improved process for the preparation of asymmetrically N-substituted diaminoethanes by reacting imines with amines in the presence of carbon dioxide.

It is known that N-alkyl- and N,N-dialkyldiaminoethanes can be prepared, for example, by aminolysis of phthalimides with subsequent hydrolysis to give the ethylenediamine derivative (DD-A-17068), by aminolysis of 2-chloroethylamine (Monatshefte der Chemie 84 (1953) 362), by reacting secondary amines with acrylamide with subsequent Hoffmann rearrangement to the diamine (Chem. Abstr. Vol. 96, 180762p, and by reacting amines, formaldehyde and hydrocyanic acid to give the N-substituted glycine nitrile, which, on hydrogenation, likewise gives the asymmetrically substituted ethylenediamine derivative desired.

The aminoethylation of an appropriate amine using ethyleneimine has been carried out with (Izw. Akad. Nauk, SSSR, Ser. Khim. 1987, 4, 946-948) and without (U.S. Application No. 2,318,729) acidic catalysis. The yields are unsatisfactory and the reaction times are too long.

In Chem. Abstr. Vol. 99, 157814 and Vol. 98, 157813, the catalyst used for the synthesis of N-methylethylenediamine and N,N-dimethylethylenediamine is methylamine or dimethylamine and ethyleneimine with 30 mol. % or 3 mol. % respectively of hydrochloric acid. The amine:ethyleneimine ratio is 5:1 (in the case of methylamine) and 3:1 (in the case of dimethylamine). The work-up is not described, and the yields, determined by gas chromatography, are from 80 to 90%.

However, the last-mentioned process relies on the use of an autoclave, since the low-boiling amines generate a pressure of from 8 to 12 bar at the prescribed reaction temperature of from 110° to 140° C. Moreover, the use of hydrochloric acid is disadvantageous due to the associated corrosion problems. Since the added hydrochloric acid must be neutralized during work-up in order to liberate the product completely, considerable amounts of, for example, sodium chloride are sometimes produced in the reaction described.

It is an object of the present invention to find a process for the preparation of asymmetrically substituted diaminoethane derivatives which remedies the abovedescribed disadvantages.

We have found that this object is achieved by a novel and improved process for the preparation of an N-alkyl- or N,N-dialkyl-1,2-diaminoethane of the general formula I

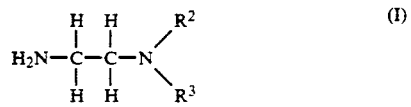

where $R^1$ is hydrogen or methyl, $R^2$ is $C_1$- to $C_5$-alkyl, and $R^3$ is hydrogen or $C_1$- to $C_5$-alkyl, with the proviso that the total number of carbon atoms in $R^2$ and $R^3$ is an integer from 1 to 6, by reacting an imine of the general formula II

with an amine to the general formula III

where $R^1$, $R^2$ and $R^3$ are as defined above, which comprises carrying out the reaction in the presence of carbon dioxide at from 10° to 150° C. and at from 0.5 to 50 bar, preferably at from 1 to 10 bar.

The compounds I can be prepared by the following method:

Carbon dioxide is added to the amine (III) to be reacted, either as such or in a solvent. The amount of $CO_2$ is from 0.1 to 2.0 mol equivalents, based on the alkyleneimine (II) to be reacted. Suitable solvents are water, alcohols and all liquids which are inert under the reaction conditions.

The carbon dioxide can be added either in solid form or as a gas.

The alkyleneimine (II) is then added to the reaction solution The alkyleneimine (II):amine (III) molar ratio is from 1:1 to 0.1:1, preferably from 1:1 to 0.25:1. In many cases, the excess amine can easily be recovered when the reaction is complete Like the amine, the alkyleneimine can also be employed as such or as a solution of various concentrations. The solvent content in the reaction batch can be from 0% to 90%.

The time taken for the addition is from 0.25 to 10 hours, preferably from 2 to 4 hours.

The reaction temperature is kept at from 10° C. to 150° C., and has an upper limit of the reflux temperature of the batch; the preferred temperature is just below the boiling point of the reaction batch. The reaction temperature can be varied during the reaction, but may alternatively be kept constant. The reaction is carried out at from 0.5 to 50 bar, preferably at from 0.1 to 5 bar, particularly preferably at atmospheric pressure.

When the alkyleneimine has been added, the mixture is stirred for from 1 to 10 hours. The temperature conditions applying are as above.

When the reaction is complete, from 1 to 20 mol, preferably from 2 to 4 mol, of an alkali metal hydroxide or alkaline earth metal hydroxide are added to the reaction batch per mole of carbon dioxide.

The batch prepared in this way is subsequently worked up by distillation. For an aqueous system, it is also possible to remove the water in advance by adding an alkali metal hydroxide or alkaline earth metal hydroxide or a concentrated aqueous solution thereof and to subsequently distil the dried batch in order to purify the crude product, if necessary.

Particularly suitable amines for reacting with ethyleneimine or propyleneimine by the process according to the invention are those having from 1 to 6 carbon atoms as the total number for $R^2$ and $R^3$, such as methylamine, ethylamine, propylamine, dimethylamine, methylethylamine, methylpropylamine, diethylamine, ethylpropylamine and dipropylamine.

The N-alkyl- and N,N-dialkyl-1,2-aminoethanes are valuable intermediates for active compounds for drugs.

PREPARATION EXAMPLES

Example 1

912 g of 59.2% strength aqueous dimethylamine solution (12 mol) were introduced into a flask fitted with reflux condenser (brine, $< -10°$ C.), stirrer, dropping funnel and internal thermometer. 88 g (2 mol) of carbon dioxide in gaseous form were subsequently passed into this solution. When all the carbon dioxide had been added, 287 g of a 60% strength aqueous ethyleneimine solution (4 mol) were added at a uniform rate over the course of 2 hours. The batch was kept at from 38° to 40° C.

When the ethyleneimine addition was complete, the mixture was stirred at 48° C. for a further 6 hours. For work-up, the brine cooling in the condenser was replaced by cooling water. 448 g of 50% strength potassium hydroxide solution were subsequently stirred into the reaction mixture, and the batch was heated, when the addition was completed, to the reflux temperature (about 107° C.), where it was kept for 0.25 hours. The batch was then cooled to 50° C., and the clear, colorless lower phase was separated off. The upper phase was subsequently treated with 300 g of caustic soda and stirred at 70° C. for 0.5 hours, the phases were allowed to separate, and the lower phase was separated off.

The upper phase was treated with two portions of 15 g of caustic soda and stirred at from 70° to 80° C. for 0.25 hours. The crude product was subsequently distilled under reduced pressure. 275 g of colorless distillate were collected in the receiver.

Yield: 275 g of N,N-dimethylaminoethylamine (78%, based on ethyleneimine)
Content: 98.6% (GC)
Amine number: 22.40 mmol/g (99% of theory)
Water content: 0.3%
Tert. nitrogen: 11.19 mmol/g (98.4% of theory)
Refractive index (25° C.): 1.4251 (lit.: 1.4250 at 25° C.)
Elemental analysis:
Calc. C=54.56 H=13.72 N=31.78;
Found C=54.4 H=13.4 N=31.5

Example 2

66 g (1.5 mol) of gaseous carbon dioxide were introduced into 282 g of 64% strength aqueous DMA solution (4 mol) in the apparatus described in Example 1, and 143 g of 60% strength aqueous ethyleneimine solution (2 mol) were added dropwise at from 60° to 66° C. over the course of 2 hours, the mixture was stirred for a further 1 hour, 480 g of 50% strength sodium hydroxide solution were added dropwise, and the mixture was then stirred at 90° C. for 1 hour, during which excess DMA evaporated off.

After the reaction batch had separated into two phases, the upper phase was treated with 73 g of caustic soda and distilled at from 50° to 60° C. under reduced pressure.

Yield: 74 g of N,N-dimethylaminoethylamine (42%, based on ethyleneimine)
Content: 99%
Water content: 0.6%

Example 3

44 g (1 mol) of gaseous carbon dioxide were added to 876 g of 60% strength aqueous tert-butylamine solution (6 mol) in the apparatus described in Example 1, and 143 g of 60% strength aqueous ethyleneimine solution (2 mol) were added dropwise at 70° C. over the course of 2 hours, the mixture was stirred at 70° C. for a further 5 hours, 320 g of 50% strength sodium hydroxide solution were added dropwise, and the batch was heated to 110° C., during which a tert-butylamine/water mixture distilled over. The distillation was terminated at a transition temperature of 100° C., the lower phase of the two-phase batch was separated off, and the water was removed from the upper phase at 90° C. as usual using $3 \times 40$ ml of 50% strength sodium hydroxide solution.

The GC of the crude product (155 g) showed a content of 77% of tert-butylaminoethylamine.

Example 4

44 g of carbon dioxide (1 mol) were added to 730 g of 60% strength aqueous diethylamine solution (6 mol) in the apparatus described in Example 1, and 143 g of 60% strength aqueous ethyleneimine solution (2 mol) were added at an internal temperature of 38° C. over the course of 2 hours.

The mixture was subsequently stirred at 70° C. for a further 4 hours and treated with 247 g of 50% strength potassium hydroxide solution, the excess diethylamine was removed by distillation to an internal temperature of 98° C., the two-phase reaction batch was cooled to 50° C., and the lower phase was separated off.

After the upper phase had been dried using caustic soda and the phases had subsequently been separated, the crude product was distilled over caustic soda at a transition temperature of from 45° to 65° C. under reduced pressure.

Yield: 117 g of N,N-diethylaminoethylamine (50%, based on ethyleneimine)
Content: 97% (GC)

Example 5

44 g of carbon dioxide (1 mol) were added to 383 g of 71% strength aqueous ethylamine solution (6 mol) in the apparatus described in Example 1, and 143 g of 60 strength aqueous ethyleneimine solution (2 mol) were added at an internal temperature of from 40° to 50° c. over the course of 2 hours.

The mixture was subsequently stirred at 55° C. for a further 6 hours, treated with 244 g of 50% strength potassium hydroxide solution and heated to an internal temperature of 107°0 C., during which the excess diethylamine was removed. The two-phase reaction batch was cooled to 50° C., and the lower phase was separated off.

The upper phase was treated with 105 g of caustic soda, and the lower phase was subsequently separated off. The crude product (123 g, water content 2%) contained 71% of ethylaminoethylamine (GC).

We claim:.

1. A process for the preparation of an N-alkyl- or N,N-dialkyl-1,2-diaminoethane of the formula

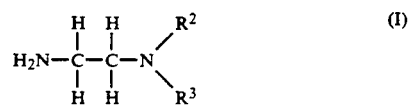

where $R^1$ is hydrogen or methyl, $R^2$ is $C_1$- to $C_5$-alkyl, and $R^3$ is hydrogen or $C_1$- to $C_5$-alkyl, with the proviso that the total number of carbon atoms in $R^2$ and $R^3$ is an integer from 1 to 6, by reacting an imine of the formula

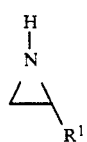 (II)

with an amine of the formula

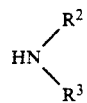 (III)

where $R^1$, $R^2$ and $R^3$ are as defined above, which comprises carrying out the reaction in the presence of added carbon dioxide at from 10° to 150° C. and at from 0.5 to 50 bar.

2. A process as claimed in claim 1, wherein the imine II and the amine III are employed in a molar ratio of from 1:1 to 0.1:1.

3. A process as claimed in claim 1, wherein the imine II and the amine III are employed in a molar ratio of from 1:1 to 0.25:1.

4. A process as claimed in claim 1, wherein from 0.1 to 2 mol equivalents of carbon dioxide are used, based on the imine employed.

5. A process as claimed in claim 1, wherein the reaction is carried out at from 1 to 10 bar.

6. A process as claimed in claim 1, wherein the alkyleneimine reactant II is selected from the gorup consisting of ethyleneimine and propyleneimine.

7. A process as claimed in claim 1, wherein the amine reactant III is selected from the group consisting of methylamine, ethylamine, propylamine, dimethylamine, methylethylamine, methylpropylamine, diethylamine, ethylpropylamine and dipropylamine.

8. A process as claimed in claim 1, wherein the reaction is carried out in an inert solvent.

9. A process as claimed in claim 1, wherein the reaction is carried out in water as an inert solvent.

10. A process as claimed in claim 1, wherein ethyleneimine is reacted with dimethylamine.

11. A process as claimed in claim 1, wherein ethyleneimine is reacted with tert-butylamine.

* * * * *

UNITED STATES PATENT AND TRADEMARK OFFICE
CERTIFICATE OF CORRECTION

PATENT NO. : 5,158,974
DATED : October 27, 1992
INVENTOR(S) : Hohmann et al.

It is certified that error appears in the above-identified patent and that said Letters Patent is hereby corrected as shown below:

Title page, item [57]

IN THE ABSTRACT:

Please correct formula (I) to read as follows:

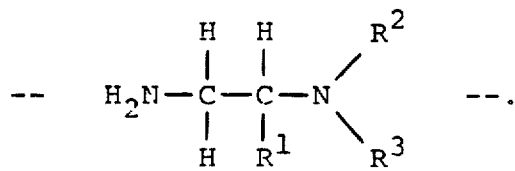

Column 4,

Claim 1: Please also correct formula (I) to read as appears above in the abstract.

Column 6,

Claim 6, line 2: change "gorup" to --group--.

Signed and Sealed this

Nineteenth Day of October, 1993

Attest:

BRUCE LEHMAN

Attesting Officer

Commissioner of Patents and Trademarks